(12) United States Patent
Takahashi

(10) Patent No.: US 12,215,270 B2
(45) Date of Patent: Feb. 4, 2025

(54) AZEOTROPIC OR AZEOTROPIC-LIKE COMPOSITION COMPRISING 2-CHLORO-1,1-DIFLUOROETHANE

(71) Applicant: DAIKIN INDUSTRIES, LTD., Osaka (JP)

(72) Inventor: Kazuhiro Takahashi, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 182 days.

(21) Appl. No.: 17/376,787

(22) Filed: Jul. 15, 2021

(65) Prior Publication Data

US 2021/0340084 A1 Nov. 4, 2021

Related U.S. Application Data

(63) Continuation of application No. PCT/JP2020/001281, filed on Jan. 16, 2020.

(30) Foreign Application Priority Data

Jan. 16, 2019 (JP) .................. 2019-005305

(51) Int. Cl.
*C09K 5/04* (2006.01)
*C07C 19/12* (2006.01)
*C11D 7/50* (2006.01)

(52) U.S. Cl.
CPC .............. *C09K 5/044* (2013.01); *C07C 19/12* (2013.01); *C09K 5/045* (2013.01); *C11D 7/5045* (2013.01); C09K 2205/122 (2013.01); C09K 2205/126 (2013.01); C09K 2205/32 (2013.01)

(58) Field of Classification Search
CPC ....... C07C 19/12; C07C 19/05; C07C 21/073; C07C 21/18; C09K 5/045; C09K 2205/122; C09K 2205/126; C09K 2205/32; C09K 5/044; C09K 5/04; C09K 5/041; C09K 2205/22; C11D 7/5045; C11D 7/5059; C11D 7/30; C11D 3/24; C11D 3/245; C11D 7/5018; C11D 7/5036; C11D 7/504; C11D 7/5054; C08J 9/14; C08J 9/143; C08J 9/144; C08J 9/149
USPC ......................................................... 252/67
See application file for complete search history.

(56) References Cited

U.S. PATENT DOCUMENTS

| | | | | |
|---|---|---|---|---|
| 5,137,929 | A * | 8/1992 | Demmin | C08J 9/144 252/68 |
| 6,403,550 | B1 * | 6/2002 | Bolmer | C11D 7/5045 510/415 |
| 10,029,961 | B2 * | 7/2018 | Deur-Bert | C07C 19/08 |
| 2012/0014897 | A1 * | 1/2012 | Banowski | A61K 8/37 424/65 |
| 2014/0077123 | A1 * | 3/2014 | Fukushima | C09K 5/044 570/136 |
| 2016/0002518 | A1 * | 1/2016 | Taniguchi | C07C 17/278 252/67 |
| 2016/0347693 | A1 * | 12/2016 | Fukushima | C07C 17/354 |
| 2017/0267612 | A1 * | 9/2017 | Bonnet | C07C 17/206 |
| 2018/0029962 | A1 * | 2/2018 | Garrait | C07C 17/383 |
| 2019/0300473 | A1 * | 10/2019 | Garrait | C07C 209/08 |
| 2020/0002253 | A1 * | 1/2020 | Garrait | C07C 17/383 |
| 2021/0309594 | A1 * | 10/2021 | Garrait | C07C 17/206 |
| 2021/0403778 | A1 * | 12/2021 | Takahashi | C09K 5/044 |
| 2023/0138340 | A1 * | 5/2023 | Kushida | C07C 17/25 570/230 |

FOREIGN PATENT DOCUMENTS

| | | | | |
|---|---|---|---|---|
| FR | 3014105 A1 * | 6/2015 | ......... | C07C 17/206 |
| JP | 2016130236 A * | 7/2016 | ......... | C07C 17/383 |
| WO | 2012/157765 | 11/2012 | | |
| WO | WO-2018060575 A1 * | 4/2018 | ......... | C07C 19/12 |
| WO | WO-2018060576 A1 * | 4/2018 | ......... | C07C 17/206 |
| WO | WO-2018069609 A1 * | 4/2018 | ......... | C07C 17/206 |

OTHER PUBLICATIONS

CAS reg. No. 2268-32-8, Nov. 16, 1984. (Year: 1984).*
CAS reg. No. 338-65-8, Nov. 16, 1984. (Year: 1984).*
International Search Report issued Apr. 7, 2020 in International (PCT) Application No. PCT/JP2020/001281.

* cited by examiner

*Primary Examiner* — Matthew R Diaz
(74) *Attorney, Agent, or Firm* — WENDEROTH, LIND & PONACK, L.L.P.

(57) ABSTRACT

It is an object to provide a new azeotropic or azeotropic-like composition comprising HCFC-142. The present disclosure provides, as its solution, an azeotropic or azeotropic-like composition comprising a refrigerant, wherein the refrigerant comprises 2-chloro-1,1-difluoroethane (HCFC-142) and at least one additional compound selected from the group consisting of trans-1,2-dichloroethylene (HCO-1130(E)) and the like.

4 Claims, No Drawings

AZEOTROPIC OR AZEOTROPIC-LIKE COMPOSITION COMPRISING 2-CHLORO-1,1-DIFLUOROETHANE

TECHNICAL FIELD

The present disclosure relates to an azeotropic or azeotropic-like composition comprising 2-chloro-1,1-difluoroethane.

BACKGROUND ART

Refrigerants comprising E- and Z-1,2-difluoroethylene (E-HFO-1132 and Z-HFO-1132) are very promising as alternative substances to refrigerants used in air conditioners in which HFC-410A, HFC-32, HFC-134a, and the like have been used so far (Patent Literature 1).

CITATION LIST

Patent Literature

PTL 1: International Publication No. WO 2012/157765

SUMMARY

Item 1.
An azeotropic or azeotropic-like composition comprising a refrigerant, wherein
the refrigerant comprises
2-chloro-1,1-difluoroethane (HCFC-142), and
at least one additional compound selected from the group consisting of trans-1,2-dichloroethylene (HCO-1130 (E)), cis-1,2-dichloroethylene (HCO-1130(Z)), 1,1,2-trichloroethane (HCO-140), 1,2-dichloro-1-fluoroethane (HCFC-141), trans-1-chloro-2-fluoroethylene (HCFO-1131(E)), trans-1-chloro-2-fluoroethylene (HCFO-1131(Z)), 1-chloro-1,2-difluoroethylene (HCFO-1122a), 1-chloro-1,2,2-trifluoroethane (HCFC-133), and 1-chloro-1,1,2-trifluoroethane (HCFC-133b).

The present disclosure provides a new azeotropic or azeotropic-like composition.

DESCRIPTION OF EMBODIMENTS

Definitions of Terms

As used herein, the term "refrigerant" includes at least compounds to which refrigerant numbers beginning with R representing the types of refrigerants (ASHRAE numbers) specified in ISO 817 (International Organization for Standardization) are given, and further includes those having properties as a refrigerant equivalent to the properties of the compounds even if refrigerant numbers are not yet given. Refrigerants are broadly divided into "fluorocarbon-based compounds" and "non-fluorocarbon-based compounds" in terms of the structures of the compounds. The "fluorocarbon-based compounds" include a chlorofluorocarbon (CFC), a hydrochlorofluorocarbon (HCFC), and a hydrofluorocarbon (HFC). Examples of the "non-fluorocarbon-based compounds" include propane (R290), propylene (R1270), butane (R600), isobutane (R600a), carbon dioxide (R744), and ammonia (R717).

As used herein, the term "composition comprising a refrigerant" includes at least (1) a refrigerant itself (including a mixture of refrigerants), (2) a composition that further comprises other components and can be used for obtaining a working fluid for a refrigerator by being mixed with at least a refrigerator oil, and (3) a working fluid for a refrigerator containing a refrigerator oil. As used herein, of these three embodiments, the composition of (2) is referred to as a "refrigerant composition" as distinguished from a refrigerant itself (including a mixture of refrigerants). The working fluid for a refrigerator of (3) is referred to as a "refrigerator oil-containing working fluid" as distinguished from a "refrigerant composition".

As used herein, the term "azeotropic-like composition" means a composition that can be handled in substantially the same manner as an azeotropic composition. Specifically, as used herein, the term "azeotropic-like composition" means a constant boiling point mixture or substantially constant boiling point mixture of two or more substances that behave as a substantially single substance. An example of one of the features of the azeotropic-like composition includes the fact that the composition of a vapor generated by the evaporation or distillation of a liquid is substantially unchanged from the composition of the liquid. In other words, as used herein, when a certain mixture boils, distills, or refluxes without a substantial composition change, this mixture is referred to as an azeotropic-like composition. Specifically, when the difference between the bubble point vapor pressure of a composition and the dew point vapor pressure of the composition at a certain particular temperature is 3% or less (based on the bubble point pressure), the composition is defined as an azeotropic-like composition in the present disclosure.

As used herein, when the term "alternative" is used in the context in which a second refrigerant is "alternative" to a first refrigerant, as a first type, it means that equipment designed for operation using the first refrigerant can be operated under optimum conditions using the second refrigerant, by undergoing only the change of a few parts (at least one of a refrigerator oil, a gasket, packing, an expansion valve, a dryer, and other parts) and equipment adjustment as needed. In other words, this type of alternative indicates that the same equipment is operated with an "alternative" refrigerant. Embodiments of this type of "alternative" can be a "drop in alternative", a "nearly drop in alternative", and a "retrofit" in the order in which the extent of changes or adjustment necessary for replacement with the second refrigerant is smaller.

The term "alternative" also includes, as a second type, using equipment designed for operation using the second refrigerant, with the second refrigerant mounted, for the same application as an existing application of the first refrigerant. This type of alternative indicates that the same application is achieved with an "alternative" refrigerant.

As used herein, the term "refrigerator" refers to an apparatus in general that takes the heat of an object or space away to set the temperature lower than that of the ambient outside air, and maintains this low temperature. In other words, the refrigerator refers to a conversion apparatus that obtains energy from the outside, works, and converts the energy in order to transfer heat from where the temperature is lower to where the temperature is higher.

The present inventor has found that in a method for producing HFC-143, the raw materials used are not all converted into the target and need to be separated and recovered by some method for recycle. The present inventor has paid attention to the fact that HCFC-142 is a useful intermediate in this process, and unless it is recovered, these raw materials are lost, leading to cost increase.

The present inventor has found that this HCFC-142 forms an azeotropic or azeotropic-like composition with at least one intermediate substance selected from the group consisting of trans-1,2-dichloroethylene, cis-1,2-dichloroethylene, 1-chloro-1,2,2-trifluoroethane (HCFC-133), and 1-chloro-1,1,2-trifluoroethane (HCFC-133b). Further, the present inventor has thought of an HCFC-142 separation and recovery process using this azeotropic or azeotropic-like composition.

1. Azeotropic or Azeotropic-Like Composition

The azeotropic or azeotropic-like composition of the present disclosure is an azeotropic or azeotropic-like composition comprising a refrigerant, wherein the refrigerant comprises HCFC-142 and at least one additional compound (additional compound 1) selected from the group consisting of trans-1,2-dichloroethylene, cis-1,2-dichloroethylene, 1,1,2-trichloroethane, trans-1-chloro-2-fluoroethylene (HCFO-1131(E)), trans-1-chloro-2-fluoroethylene (HCFO-1131(Z)), 1-chloro-1,2-difluoroethylene (HCFO-1122a), 1,2-dichloro-1-fluoroethane (HCFC-141), 1-chloro-1,2,2-trifluoroethane (HCFC-133), and 1-chloro-1,1,2-trifluoroethane (HCFC-133b).

The azeotropic or azeotropic-like composition of the present disclosure preferably comprises 85% by mass or more, more preferably 95% by mass or more, and further preferably 99% by mass or more of HCFC-142 based on the entire refrigerant in terms of superior stability.

The azeotropic or azeotropic-like composition of the present disclosure may further comprise another additional compound (additional compound 2) in addition to HCFC-142 and additional compound 1.

For example, additional compound 2 may be at least one additional compound selected from the group consisting of 1,1,2-trifluoroethylene (HFO-1123), 1,1-difluoromethane, fluoroethane, 1,1,2-trifluoroethane (HFC-143), 2,2-dichloro-1,1,1-trifluoroethane (HCFC-123), and 1,2-difluoroethane (HFC152).

The azeotropic or azeotropic-like composition of the present disclosure preferably comprises more than 0% by mass and 30% by mass or less, more preferably more than 0% by mass and 10% by mass or less, and further preferably more than 0% by mass and 1% by mass or less of additional compound 2 in total based on the entire composition in that additional compound 2 does not inhibit the composition containing HCFC-142 and additional compound 1 from being an azeotropic or azeotropic-like composition.

The total content and types of the additional compounds can be appropriately selected within a range in which they do not inhibit composition 1 containing a mixture of HCC-140 and hydrogen fluoride that is an azeotropic or azeotropic-like composition from being an azeotropic or azeotropic-like composition.

The azeotropic or azeotropic-like composition of the present disclosure can be used, for example, as a heat transfer medium, a foaming agent, a cleaning agent, or a solvent, although not limited thereto.

2. Heat Transfer Medium Composition

When the composition of the present disclosure is used as a heat transfer medium composition, it can also be used as a refrigerant having a lower global warming potential (GWP) that is alternative to a refrigerant such as HFC134a, HFC410A, HFC407C, or HFC404A, which is a conventionally used HFC refrigerant, or as a component of the above refrigerant.

The composition of the present disclosure used as a heat transfer medium composition may further contain at least one other component in addition to the additional compounds. The composition of the present disclosure can be further used for obtaining a working fluid for a refrigerator by being mixed with at least a refrigerator oil (the composition of the present disclosure in this case is referred to as "the refrigerant composition of the present disclosure").

The refrigerant composition of the present disclosure may contain at least one of the other components described below as needed. The other components are not limited, and specific examples include water, a tracer, an ultraviolet fluorescent dye, a stabilizer, and a polymerization inhibitor.

When the refrigerant composition of the present disclosure is used as a working fluid in a refrigerator, it is usually used by being mixed with at least a refrigerator oil. Therefore, the refrigerant composition of the present disclosure is preferably substantially free from a refrigerator oil. Specifically, in the refrigerant composition of the present disclosure, the content of a refrigerator oil based on the entire composition is preferably 0 to 1% by mass, more preferably 0 to 0.1% by mass.

The refrigerant composition of the present disclosure may comprise a slight amount of water. The water content in the refrigerant composition is preferably 0.1% by mass or less based on an entirety of the refrigerant. When the refrigerant composition comprises a slight amount of water, the intramolecular double bond of the unsaturated fluorocarbon-based compound that can be contained in the refrigerant is stabilized, and the oxidation of the unsaturated fluorocarbon-based compound is also less likely to occur, and therefore the stability of the refrigerant composition improves.

The tracer is added to the refrigerant composition of the present disclosure at a detectable concentration so that when the refrigerant composition of the present disclosure is diluted or contaminated or undergoes some other change, the change can be traced.

The refrigerant composition of the present disclosure may contain one tracer alone or may contain two or more tracers.

The tracer is not limited and can be appropriately selected from generally used tracers.

Examples of the tracer include a hydrofluorocarbon, a hydrochlorofluorocarbon, a chlorofluorocarbon, a hydrochlorocarbon, a fluorocarbon, a deuterated hydrocarbon, a deuterated hydrofluorocarbon, a perfluorocarbon, a fluoroether, a brominated compound, an iodinated compound, an alcohol, an aldehyde, a ketone, and nitrous oxide ($N_2O$). As the tracer, a hydrofluorocarbon, a hydrochlorofluorocarbon, a chlorofluorocarbon, a hydrochlorocarbon, a fluorocarbon, and a fluoroether are particularly preferred.

As the tracer, the following compounds are preferred: FC-14 (tetrafluoromethane, $CF_4$), HCC-40 (chloromethane, $CH_3Cl$), HFC-23 (trifluoromethane, $CHF_3$), HFC-41 (fluoromethane, $CH_3Cl$), HFC-125 (pentafluoroethane, $CF_3CHF_2$), HFC-134a (1,1,1,2-tetrafluoroethane, $CF_3CH_2F$), HFC-134 (1,1,2,2-tetrafluoroethane, $CHF_2CHF_2$), HFC-143a (1,1,1-trifluoroethane, $CF_3CH_3$), HFC-152 (1,2-difluoroethane, $CH_2FCH_2F$), HFC-245fa (1,1,1,3,3-pentafluoropropane, $CF_3CH_2CHF_2$), HFC-236fa (1,1,1,3,3,3-hexafluoropropane, $CF_3CH_2CF_3$), HFC-236ea (1,1,1,2,3,3-hexafluoropropane, $CF_3CHFCHF_2$), HFC-227ea (1,1,1,2,3,3,3-heptafluoropropane, $CF_3CHFCF_3$), HCFC-22 (chlorodifluoromethane, $CHClF_2$), HCFC-31 (chlorofluoromethane, $CH_2ClF$), CFC-1113 (chlorotrifluoroethylene, $CF_2=CClF$), HFE-125 (trifluoromethyl-difluoromethyl ether, $CF_3OCHF_2$), HFE-134a (trifluoromethyl-fluoromethyl ether, $CF_3OCH_2F$), HFE-143a (trifluoromethyl-methyl ether, $CF_3OCH_3$), HFE-227ea (trifluoromethyl-tetrafluoroethyl ether, $CF_3OCHFCF_3$), and HFE-236f a (trifluoromethyl-trifluoroethyl ether, $CF_3OCH_2CF_3$).

The refrigerant composition of the present disclosure may comprise about 10 parts per million (ppm) by weight to about 1,000 ppm of the tracer in total based on the entire refrigerant composition. The refrigerant composition of the present disclosure may comprise preferably about 30 ppm to about 500 ppm, more preferably about 50 ppm to about 300 ppm, of the tracer in total based on the entire refrigerant composition.

The refrigerant composition of the present disclosure may contain one ultraviolet fluorescent dye alone or may contain two or more ultraviolet fluorescent dyes.

The ultraviolet fluorescent dye is not limited and can be appropriately selected from generally used ultraviolet fluorescent dyes.

Examples of the ultraviolet fluorescent dye include naphthalimide, coumarin, anthracene, phenanthrene, xanthene, thioxanthene, naphthoxanthene, and fluorescein, and derivatives thereof. As the ultraviolet fluorescent dye, either or both of naphthalimide and coumarin are particularly preferred.

The refrigerant composition of the present disclosure may contain one stabilizer alone or may contain two or more stabilizers.

The stabilizer is not limited and can be appropriately selected from generally used stabilizers.

Examples of the stabilizer include nitro compounds, ethers, and amines.

Examples of the nitro compounds include aliphatic nitro compounds such as nitromethane and nitroethane, and aromatic nitro compounds such as nitrobenzene and nitrostyrene.

Examples of the ethers include 1,4-dioxane.

Examples of the amines include 2,2,3,3,3-pentafluoropropylamine and diphenylamine.

Other examples include butylhydroxyxylene and benzotriazole.

The content of the stabilizer is not limited and is usually preferably 0.01 to 5% by mass, more preferably 0.05 to 2% by mass based on an entirety of the refrigerant.

The refrigerant composition of the present disclosure may contain one polymerization inhibitor alone or may contain two or more polymerization inhibitors.

The polymerization inhibitor is not limited and can be appropriately selected from generally used polymerization inhibitors.

Examples of the polymerization inhibitor include 4-methoxy-1-naphthol, hydroquinone, hydroquinone methyl ether, dimethyl-t-butylphenol, 2,6-di-tert-butyl-p-cresol, and benzotriazole.

The content of the polymerization inhibitor is not limited and is usually preferably 0.01 to 5% by mass, more preferably 0.05 to 2% by mass based on an entirety of the refrigerant.

The composition of the present disclosure can also be used as a working fluid for a refrigerator containing a refrigerator oil (this composition is referred to as "the refrigerator oil-containing working fluid of the present disclosure"). The refrigerator oil-containing working fluid of the present disclosure comprises at least the refrigerant composition of the present disclosure and a refrigerator oil and is used as a working fluid in a refrigerator. Specifically, the refrigerator oil-containing working fluid of the present disclosure is obtained by the mixing of a refrigerator oil used in the compressor of a refrigerator and the refrigerant or the refrigerant composition with each other. The refrigerator oil-containing working fluid generally contains 10 to 50% by mass of the refrigerator oil.

The refrigerator oil-containing working fluid of the present disclosure may contain one refrigerator oil alone or may contain two or more refrigerator oils.

The refrigerator oil is not limited and can be appropriately selected from generally used refrigerator oils. At the time, a refrigerator oil which is superior in terms of miscibility with the mixture and the function of improving the stability of the mixture and the like can be appropriately selected as needed.

As the base oil of the refrigerator oil, for example, at least one selected from the group consisting of a polyalkylene glycol (PAG), a polyol ester (POE), and a polyvinyl ether (PVE) is preferred.

The refrigerator oil may further comprise an additive in addition to the base oil. The additive may be at least one selected from the group consisting of an antioxidant, an extreme pressure agent, an acid scavenger, an oxygen scavenger, a copper deactivator, a rust preventive, an oily agent, and an antifoaming agent.

As the refrigerator oil, one having a kinematic viscosity of 5 to 400 cSt at 40° C. is preferred in terms of lubrication.

The refrigerator oil-containing working fluid of the present disclosure may further comprise at least one additive as needed. Examples of the additive include the following compatibilizing agent.

The refrigerator oil-containing working fluid of the present disclosure may contain one compatibilizing agent alone or may contain two or more compatibilizing agents.

The compatibilizing agent is not limited and can be appropriately selected from generally used compatibilizing agents.

Examples of the compatibilizing agent include a polyoxyalkylene glycol ether, an amide, a nitrile, a ketone, a chlorocarbon, an ester, a lactone, an aryl ether, a fluoroether, and a 1,1,1-trifluoroalkane. As the compatibilizing agent, a polyoxyalkylene glycol ether is particularly preferred.

3. Separation Method

The azeotropic or azeotropic-like composition of the present disclosure can be an important composition when azeotropic distillation for separating additional compound 1 from HCFC-142 in a mixture of HCFC-142 and additional compound 1 is performed.

Azeotropic distillation is a method of concentrating or separating a target by operating a distillation column under such conditions that an azeotropic or azeotropic-like composition is separated. Only a component to be separated can be distilled by azeotropic distillation in some cases, but azeotropic distillation occurs only after another component that forms an azeotrope with one or more components to be separated is externally added, in some cases. In a narrow sense, only the latter is referred to as azeotropic distillation. For example, additional compound 1 can be separated from HCFC-142 by extracting an azeotropic or azeotropic-like composition comprising HCFC-142 and additional compound 1 from a composition comprising at least HCFC-142 and additional compound 1 by azeotropic distillation.

Item 1.

An azeotropic or azeotropic-like composition comprising a refrigerant, wherein
the refrigerant comprises
2-chloro-1,1-difluoroethane (HCFC-142), and
at least one additional compound selected from the group consisting of trans-1,2-dichloroethylene (HCO-1130 (E)), cis-1,2-dichloroethylene (HCO-1130(Z)), 1,1,2-trichloroethane (HCO-140), 1,2-dichloro-1-fluoroethane (HCFC-141), trans-1-chloro-2-fluoroethylene (HCFO-1131(E)), trans-1-chloro-2-fluoroethylene (HCFO-1131(Z)), 1-chloro-1,2-difluoroethylene (HCFO-1122a), 1-chloro-1,2,2-trifluoroethane (HCFC-133), and 1-chloro-1,1,2-trifluoroethane (HCFC-133b).

Item 2.

The azeotropic or azeotropic-like composition according to Item 1, comprising 85% by mass or more of HCFC-142 based on an entirety of the refrigerant.

Item 3.

The azeotropic or azeotropic-like composition according to Item 1 or 2, wherein the refrigerant further comprises at least one additional compound selected from the group consisting of 1,1,2-trifluoroethylene (HFO-1123), 1,1-difluoromethane, fluoroethane, 1,1,2-trifluoroethane (HFC-143), 2,2-dichloro-1,1,1-trifluoroethane (HCFC-123), and 1,2-difluoroethane (HFC152).

Item 4.

The azeotropic or azeotropic-like composition according to any one of Items 1 to 3, used as a heat transfer medium, a foaming agent, a cleaning agent, or a solvent.

Advantageous Effects

Embodiments have been described above, and it will be understood that various changes in form and details can be made without departing from the spirit and scope of the claims.

EXAMPLES

Example 1

Vapor-liquid equilibrium data at 40° C. for
mixtures of 2-chloro-1,1-difluoroethane (HCFC-142) and
   trans-1,2-dichloroethylene (HCFO-1130(E)) (Table 1),
mixtures of 2-chloro-1,1-difluoroethane (HCFC-142) and
   cis 1,2-dichloroethylene (HCFO-1130(Z)) (Table 2),
mixtures of 2-chloro-1,1-difluoroethane (HCFC-142) and
   1,1,2-trichloroethane (HCC-140) (Table 3),
mixtures of 2-chloro-1,1-difluoroethane (HCFC-142) and
   1,2-dichloro-1-fluoroethane (HCFC-141) (Table 4),
mixtures of 2-chloro-1,1-difluoroethane (HCFC-142) and
   trans-1-chloro-2-fluoroethane (HCFO-1131(E)) (Table 5),
mixtures of 2-chloro-1,1-difluoroethane (HCFC-142) and
   cis-1-chloro-2-fluoroethane (HCFO-1131(Z)) (Table 6),
mixtures of 2-chloro-1,1-difluoroethane (HCFC-142) and
   1-chloro-1,1,2-trifluoroethane (HCFO-1122a) (Table 7),
mixtures of 2-chloro-1,1-difluoroethane (HCFC-142) and
   1-chloro-1,1,2-trifluoroethane (HCFC-133b) (Table 8), and
mixtures of 2-chloro-1,1-difluoroethane (HCFC-142) and
   1-chloro-1,2,2-trifluoroethane (HCFC-133) (Table 9)
are each shown below.

TABLE 1

| Liquid phase HCFC-142 molar ratio | Vapor phase HCFC-142 molar ratio | Pressure (MPa) |
| --- | --- | --- |
| 0.05 | 0.160 | 0.136 |
| 0.1 | 0.259 | 0.147 |
| 0.2 | 0.379 | 0.162 |
| 0.3 | 0.454 | 0.171 |
| 0.4 | 0.511 | 0.176 |
| 0.5 | 0.561 | 0.180 |
| 0.6 | 0.612 | 0.181 |

TABLE 1-continued

| Liquid phase HCFC-142 molar ratio | Vapor phase HCFC-142 molar ratio | Pressure (MPa) |
| --- | --- | --- |
| 0.7 | 0.670 | 0.180 |
| 0.8 | 0.742 | 0.178 |
| 0.9 | 0.843 | 0.171 |
| 0.95 | 0.912 | 0.166 |
| 0.99 | 0.980 | 0.160 |

This table shows that when the molar ratio of HCFC-142 is 0.5 or more and less than 0.9, the mixture is an azeotropic-like composition. At this time, when the molar ratio is converted into the mass ratio, the mass ratio of HCFC-142 is 51% by mass or more and less than 91% by mass. The azeotropic point occurs when the molar ratio of HCFC-142 is 0.63, and the pressure is 0.182 MPa.

TABLE 2

| Liquid phase HCFC-142 molar ratio | Vapor phase HCFC-142 molar ratio | Pressure (kPa) |
| --- | --- | --- |
| 0.05 | 0.181 | 86.3 |
| 0.10 | 0.301 | 96.4 |
| 0.20 | 0.453 | 112.1 |
| 0.30 | 0.550 | 123.8 |
| 0.40 | 0.621 | 132.7 |
| 0.50 | 0.68 | 139.8 |
| 0.60 | 0.734 | 145.6 |
| 0.70 | 0.788 | 150.5 |
| 0.80 | 0.846 | 154.4 |
| 0.90 | 0.915 | 157.3 |
| 0.95 | 0.955 | 158.2 |
| 0.99 | 0.990 | 158.6 |

This table shows that when the molar ratio of HCFC-142 is 0.9 or more, the mixture is an azeotropic-like composition. At this time, when the molar ratio is converted into the mass ratio, the mass ratio of HCFO-1131(E) is 88% by mass or more.

TABLE 3

| Liquid phase HCFC-142 molar ratio | Vapor phase HCFC-142 molar ratio | Pressure (kPa) |
| --- | --- | --- |
| 0.05 | 0.673 | 18.5 |
| 0.10 | 0.806 | 29.7 |
| 0.20 | 0.895 | 49.5 |
| 0.30 | 0.929 | 66.6 |
| 0.40 | 0.949 | 81.6 |
| 0.50 | 0.961 | 95.2 |
| 0.60 | 0.971 | 107.8 |
| 0.70 | 0.979 | 119.9 |
| 0.80 | 0.986 | 132.1 |
| 0.90 | 0.993 | 144.8 |
| 0.95 | 0.996 | 151.6 |
| 0.99 | 0.999 | 157.2 |

This table shows that when the molar ratio of HCFC-142 is 0.999 or more, the mixture is an azeotropic-like composition. At this time, when the molar ratio is converted into the mass ratio, the mass ratio of HCFC-142 is 99.9% by mass or more.

TABLE 4

| Liquid phase HCFC-142 molar ratio | Vapor phase HCFC-142 molar ratio | Pressure (kPa) |
|---|---|---|
| 0.05 | 0.251 | 34.7 |
| 0.1 | 0.412 | 41.9 |
| 0.2 | 0.607 | 55.9 |
| 0.3 | 0.722 | 69.5 |
| 0.4 | 0.799 | 82.7 |
| 0.5 | 0.853 | 95.6 |
| 0.6 | 0.895 | 108.3 |
| 0.7 | 0.929 | 120.9 |
| 0.8 | 0.956 | 133.4 |
| 0.9 | 0.980 | 146.0 |
| 0.95 | 0.990 | 152.3 |
| 0.99 | 0.998 | 157.4 |

This table shows that when the molar ratio of HCFC-142 is more than 0.99, the mixture is an azeotropic-like composition. At this time, when the molar ratio is converted into the mass ratio, the mass ratio of HCFC-142 is 99% by mass or more.

TABLE 5

| Liquid phase HCFO-1131(E) molar ratio | Vapor phase HCFO-1131(E) molar ratio | Total pressure MPa |
|---|---|---|
| 0.99 | 0.992 | 0.398 |
| 0.95 | 0.962 | 0.395 |
| 0.9 | 0.93 | 0.39 |
| 0.8 | 0.876 | 0.378 |
| 0.7 | 0.827 | 0.364 |
| 0.6 | 0.779 | 0.347 |
| 0.5 | 0.725 | 0.328 |
| 0.4 | 0.663 | 0.305 |
| 0.3 | 0.583 | 0.277 |
| 0.2 | 0.472 | 0.245 |
| 0.1 | 0.303 | 0.206 |

This table shows that when the molar ratio of HCFO-1131(E) is 0.9 or more, the mixture is an azeotropic-like composition. At this time, when the molar ratio is converted into the mass ratio, the mass ratio of HCFO-1131(E) is 88% by mass or more.

TABLE 6

| Liquid phase HCFO-1131(Z) molar ratio | Vapor phase HCFO-1131(Z) molar ratio | Total pressure MPa |
|---|---|---|
| 0.99 | 0.993 | 0.331 |
| 0.95 | 0.966 | 0.327 |
| 0.9 | 0.934 | 0.321 |
| 0.8 | 0.872 | 0.309 |
| 0.7 | 0.811 | 0.297 |
| 0.6 | 0.748 | 0.283 |
| 0.5 | 0.68 | 0.268 |
| 0.4 | 0.601 | 0.251 |
| 0.3 | 0.508 | 0.232 |
| 0.2 | 0.39 | 0.210 |
| 0.1 | 0.231 | 0.186 |

This table shows that when the molar ratio of HCFO-1131(Z) is 0.9 or more, the mixture is an azeotropic-like composition. At this time, when the molar ratio is converted into the mass ratio, the mass ratio of HCFO-1131(Z) is 88% by mass or more.

TABLE 7

| Liquid phase HCFO-1122a molar ratio | Vapor phase HCFO-1122a molar ratio | Total pressure MPa |
|---|---|---|
| 0.99 | 0.99 | 0.469 |
| 0.95 | 0.956 | 0.467 |
| 0.9 | 0.922 | 0.464 |
| 0.8 | 0.871 | 0.453 |
| 0.7 | 0.831 | 0.439 |
| 0.6 | 0.795 | 0.422 |
| 0.5 | 0.757 | 0.402 |
| 0.4 | 0.712 | 0.376 |
| 0.3 | 0.652 | 0.343 |
| 0.2 | 0.562 | 0.299 |
| 0.1 | 0.399 | 0.240 |

This table shows that when the molar ratio of HCFO-1122a is 0.9 or more, the mixture is an azeotropic-like composition. At this time, when the molar ratio is converted into the mass ratio, the mass ratio of HCFO-1122a is 90% by mass or more.

TABLE 8

| Liquid phase HCFC-142 molar ratio | Vapor phase HCFC-142 molar ratio | Total pressure MPa |
|---|---|---|
| 0.10 | 0.153 | 0.347 |
| 0.20 | 0.288 | 0.367 |
| 0.30 | 0.410 | 0.387 |
| 0.40 | 0.520 | 0.408 |
| 0.50 | 0.619 | 0.428 |
| 0.70 | 0.791 | 0.468 |
| 0.80 | 0.866 | 0.489 |
| 0.90 | 0.936 | 0.509 |
| 0.95 | 0.969 | 0.519 |
| 0.99 | 0.994 | 0.527 |

This table shows that when the molar ratio of HCFC-142 is 0.8 or more, the mixture is an azeotropic-like composition. At this time, when the molar ratio is converted into the mass ratio, the mass ratio of HCFC-142 is 77% by mass or more.

TABLE 9

| Liquid phase HCFC-142 molar ratio | Vapor phase HCFC-142 molar ratio | Total pressure MPa |
|---|---|---|
| 0.1 | 0.145 | 0.364 |
| 0.2 | 0.277 | 0.383 |
| 0.3 | 0.396 | 0.401 |
| 0.4 | 0.505 | 0.419 |
| 0.5 | 0.605 | 0.438 |
| 0.6 | 0.696 | 0.456 |
| 0.7 | 0.781 | 0.474 |
| 0.8 | 0.859 | 0.493 |
| 0.9 | 0.932 | 0.511 |
| 0.95 | 0.967 | 0.520 |
| 0.99 | 0.993 | 0.527 |

This table shows that when the molar ratio of HCFC-142 is 0.9 or more, the mixture is an azeotropic-like composition. At this time, when the molar ratio is converted into the mass ratio, the mass ratio of HCFC-142 is 88% by mass or more.

The above data show that the mixtures form azeotropic or azeotropic-like compositions in particular composition ranges, respectively.

The invention claimed is:
1. An azeotropic or azeotropic-like composition comprising a refrigerant, wherein
the refrigerant comprises

2-chloro-1,1-difluoroethane (HCFC-142), and
at least one additional compound selected from the group consisting of 1-chloro-1,2-difluoroethylene (HCFO-1122a), and 1-chloro-1,1,2-trifluoroethane (HCFC-133b),
wherein a content of the HCFC-142 is 85% by mass or more based on an entirety of the refrigerant.

2. The azeotropic or azeotropic-like composition according to claim 1, wherein the refrigerant further comprises at least one additional compound selected from the group consisting of 1,1,2-trifluoroethylene (HFO-1123), difluoromethane, fluoroethane, 1,1,2-trifluoroethane (HFC-143), 2,2-dichloro-1,1,1-trifluoroethane (HCFC-123), and 1,2-difluoroethane (HFC152).

3. The azeotropic or azeotropic-like composition according to claim 1, used as a heat transfer medium, a foaming agent, a cleaning agent, or a solvent.

4. The azeotropic or azeotropic-like composition according to claim 2, used as a heat transfer medium, a foaming agent, a cleaning agent, or a solvent.

* * * * *